United States Patent [19]
Yang et al.

[11] Patent Number: 5,401,412
[45] Date of Patent: Mar. 28, 1995

[54] METHOD AND APPARATUS FOR MONITORING BIOLOGICAL ACTIVITY IN WASTEWATER AND CONTROLLING THE TREATMENT THEREOF

[75] Inventors: Xin Yang, Holland; Jaw F. Lee, Berwyn; William B. Armiger, Wayne; Sergey K. Maneshin, Upper Holland, all of Pa.

[73] Assignee: BioChem Technology, Inc., King of Prussia, Pa.

[21] Appl. No.: 95,123
[22] Filed: Jul. 20, 1993
[51] Int. Cl.⁶ .............................................. C02F 3/00
[52] U.S. Cl. .................................. 210/605; 210/614; 210/620
[58] Field of Search ............... 210/614, 739, 745, 601, 210/605, 620, 630, 96.1

[56] References Cited

U.S. PATENT DOCUMENTS

| | | | |
|---|---|---|---|
| 3,760,829 | 9/1973 | Schuk et al. | 210/96 |
| 3,811,777 | 5/1974 | Chure | 356/318 |
| 3,925,721 | 12/1975 | Petroff | 324/5 R |
| 3,926,737 | 12/1975 | Wilson et al. | 195/108 |
| 4,246,101 | 1/1981 | Selby, III | 210/739 |
| 4,260,490 | 4/1981 | Moss et al. | 210/620 |
| 4,488,814 | 12/1984 | Johnson | 356/417 |
| 4,577,110 | 3/1986 | MacBride et al. | 356/317 |
| 4,631,530 | 12/1986 | Gasper | 210/739 |
| 4,849,330 | 7/1989 | Humphries et al. | 356/246 |
| 4,999,116 | 3/1991 | Bowers | 210/745 |
| 5,013,442 | 5/1991 | Davis et al. | 210/614 |
| 5,094,752 | 3/1992 | Davis et al. | 210/614 |
| 5,173,187 | 12/1992 | Nader et al. | 210/614 |
| 5,180,494 | 1/1993 | Yamaguchi et al. | 210/614 |
| 5,266,209 | 11/1993 | Knight et al. | 356/39 |

FOREIGN PATENT DOCUMENTS

| | | |
|---|---|---|
| 0461166B | 6/1994 | European Pat. Off. |
| 662579 | of 0000 | U.S.S.R. |
| WO92/23738 | 11/1993 | WIPO |

OTHER PUBLICATIONS

G. T. Daigger, J. A. Butz and J. P. Stephenson, *Analysis of Evaluating of Optimizing Existing Full-Scale Wastewater Treatment Plants* Wat. Sci. Tech. vol. 25, No. 4–5, pp. 103–118, 1992.

A. R. Howgrave-Graham, F. M. Wallis & P. L. Steyn, *A Bacterial Population Analysis of Granular Sludge from a Anaerobic Digester Treating a Maize-Processing Waste* Bioresource Technology 37 (1991) 149–156.

G. Holm Kristensen, P. Elberg Jergensen and M. Henze, *Characterization of Functional Microorganism Groups and Substrate in Activated Sludge and Wastewater by Aur. Nur and Our.* Wat. Sci. Tech. vol. 25, No. 6, pp. 43–57, 1992.

Tomonori Matsuo, Takashi Mino and Hiroyasu Sato, *Metabolism of Organic Substances in Anaerobic Phase of Biological Phosphate Uptake Process* Wat. Sci. Tech. vol. 25, No. 6, pp. 83–92, 1992.

Ma. del Carmen Doria-Serrano, S. González-Martinez and M. Hernández-Esparza, *Biochemical Models for Phosphate Accumulating Microorganisms* Wat. Sci. Tech. vol. 26, No. 9–11, pp. 2245–2248, 1992.

H. Spanjers and A. Klapwijk, *Continuous Estimaton of Short Term Oxygen Demand from Respiration Measurements* Wat. Sci. Tech. vol. 24, No. 7, pp. 29–32, 1991.

George Hassapis, *Biological Oxygen Demand (BOD) Monitoring by a Multiprocessing System* IEEE Transactions on Instrumentation and Measurement, vol. 40, No. 6, Dec. 1991.

D. Jenkins and V. Tandoi, *The Applied Microbiology of Enhanced Biological Phosphate Removal–Accomplishment and Needs* Wat. Res. vol. 25, No. 12, pp. 1471–1478, 1991.

S. Ghekiere, H. Bruynooghe, K. Van Steenbergen, L. Vriens, A. Van Haute and H. Verachert, *The Effects of Nitrates and Carbon Compounds on Enhanced Biological Phosphorus Removal from Wastewaters* European Water Pollution Control., vol. 1, No. 4, 1991.

A. Grabi ska-Loniewska, *Denitrification Unit Biocenosis* Wat. Res. vol. 25, No. 12, pp. 1565–1573, 1991.

Primary Examiner—Christopher Upton
Attorney, Agent, or Firm—Miller & Christenbury

[57] ABSTRACT

Apparatus and method monitors and controls biological activity of mixed liquor under anaerobic, anoxic and aerobic conditions by measuring the change of intracellular AND(P)H of the microorganisms. A wastewater treatment system is controlled in accordance with the results generated by the monitoring system.

13 Claims, 8 Drawing Sheets

Roles of NADH in BNR Process

METHOD AND APPARATUS FOR MONITORING BIOLOGICAL ACTIVITY IN WASTEWATER AND CONTROLLING THE TREATMENT THEREOF

FIELD OF THE INVENTION

The present invention relates to a method and apparatus for monitoring biological activity in wastewater and controlling the treatment thereof, and more particularly to a method and apparatus for real time monitoring the metabolic activity of microorganisms in activated sludge used in a wastewater treatment process and using the results of such monitoring to control selected aspects of the treatment process.

BACKGROUND OF THE INVENTION

The prior art has employed many devices and systems to process and purify water from industrial operations and municipal sources prior to discharging the water. Activated-sludge wastewater treatment plants (WWTP's), which are well known in the art, have been most often utilized to address this problem. Additionally, many industrial and municipal water treatment plants utilize biological systems to pre-treat their wastes prior to discharging into the usual municipal treatment plant. In these processes, the microorganisms used in the activated sludge break down or degrade contaminants for the desired water treatment. Efficient process performance and control requires quick and accurate assessment of information on the activity of microorganisms. This has proven to be a difficult task in view of the wide variety of materials and contaminants that typically enter into treatment systems. Also, variations in the quantity of wastewater being treated, such as daily, weekly or seasonal changes, can dramatically change numerous important factors in the treatment process, such as pH, temperature, dissolved oxygen, nutrients and the like, alteration of which can be highly detrimental to proper wastewater treatment. Of course, improperly treated wastewater poses serious human health dangers.

Various biological nutrient removal (BNR) processes are currently being used in wastewater treatment plants to assist in contamination degradation. In a typical BNR process, contaminants in the wastewater, such as carbon sources (measured as biological oxygen demand or BOD), ammonia, nitrates, phosphates and the like are digested by the activated sludge in anaerobic, anoxic and aerobic stages, also known in the art. In the anaerobic stage, the wastewater, with or without passing through a preliminary settlement process, is mixed with return activated sludge (RAS), sometimes hereinafter referred to as "mixed liquor," discussed hereafter.

Certain microorganisms in the RAS are capable of rapid uptake of readily biodegradable carbon sources, such as short chain fatty acids and of forming storage products such as poly-$\beta$-hydroxbutyrate (PHB) and poly-$\beta$-hydroxyvalate (PHV). The energy for this process is provided by the hydrolysis of intracellular polyphosphates. As a result of an anaerobic selector, a large portion of available carbon sources are removed by the poly-P forming microorganisms, and $PO^{-3}_4$ is released into the water phase. The rapid uptake and storage of carbonaceous substrates by poly-P forming species of microorganisms insures proper phosphate removal in later oxic processes. It also denies access of other competing organisms to the limited amount of substrates available in the wastewater under anaerobic conditions.

In most wastewater treatment plants, one or several anoxic stages are arranged in the BNR process. In the anoxic stage, denitrifiers, i.e., microbial species capable of denitrification, utilize nitrate and/or nitrite as electron acceptors and consume some of the available carbon sources during the denitrification process. $NO_x$ is stepwise reduced to nitrogen gas and released to the atmosphere in the following manner:

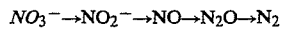

$$NO_3^- \rightarrow NO_2^- \rightarrow NO \rightarrow N_2O \rightarrow N_2$$

The nitrate is usually supplied by recycling a certain volume of wastewater at the end of the oxic stage back to the beginning of the anoxic stage.

One or several oxic stages are typically employed in BNR processes. In the oxic stage, air containing about 20% oxygen or pure oxygen, is supplied so that a desired dissolved oxygen level is maintained. Autotrophic nitrifiers, i.e., microbial species capable of using ammonia as their energy source, convert ammonia to nitrite and nitrate under aerobic conditions. The poly-P microbial species in the wastewater uptake phosphate from the water phase and digest their intracellular PHB and PHV storage products converting it into polyphosphate, a compound for energy storage. The polyphosphate pool of the poly-P microbial species is thus replenished and phosphorous is removed from the water phase. The phosphorous is then removed from the system by sludge wasting, which is well known in the art. Under aerobic conditions, the remaining carbon sources in the water phase are further digested by aerobic organisms.

Objects of the Invention

It is an object of the present invention to provide a method and apparatus for monitoring biological activity in wastewater treatment systems during anaerobic, anoxic and/or oxic stages to maximize the efficiency of the treatment process.

It is a further object of the present invention to provide a method and apparatus for real-time monitoring of the purification of wastewater to enhance control of the anaerobic, anoxic and/or oxic stages of a wastewater treatment process, to maximize process performance in response to transient and other conditions.

Other objects of the present invention will be apparent to those of ordinary skill in the art based on the following detailed description of the preferred embodiments and the appended claims.

Summary of the Invention

In accordance with the invention, the apparatus and method monitors and controls biological activity of mixed liquor under anaerobic, anoxic and aerobic conditions by measuring the change of intracellular NAD(P)H of the microorganisms. The ratio of NAD(P)H/(NAD+NAD(P)H) in the microorganisms changes during shifts in metabolic activity of the microorganisms, changes also. The corresponding change in NAD(P)H fluorescence (hereinafter sometimes referred to as "NADH") is detected and then registered by a monitoring system, such as a real time on-line computer data acquisition system, which analyzes the changes and evaluates the biological activity of the mixed liquor. The monitoring system then determines the changes in operating parameters necessary for the wastewater system to maximize the performance of the BNR processes.

A sample of the mixed liquor is pumped from a bioreactor tank to a chamber monitored by a NADH detector in the process. The sample is agitated to ensure uniform suspension of microorganisms in the wastewater and the differences in NADH quantity between the aerobic, anoxic and/or anaerobic states of the mixed liquor sample while in the chamber are registered and analyzed by the monitoring system. The mixed liquor sample is then returned to the bioreactor tank and the wastewater treatment system is controlled in accordance with the results generated by the monitoring system.

DETAILED DESCRIPTION OF THE INVENTION

Figure 1:
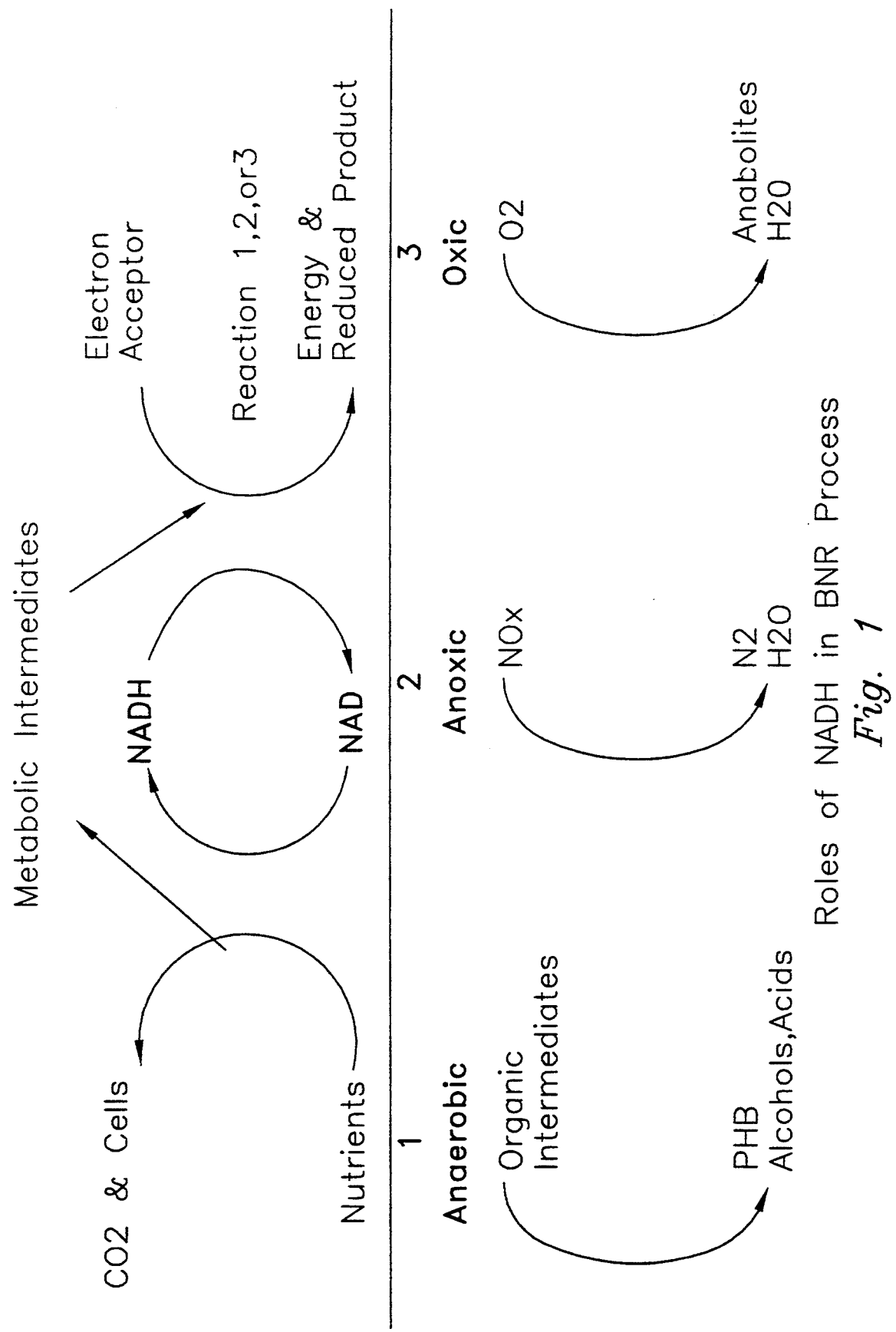
FIG. 1 is a schematic depicting the roles of NADH in a BNR process during anaerobic, anoxic and oxic stages of a wastewater treatment process.
Figure 2:
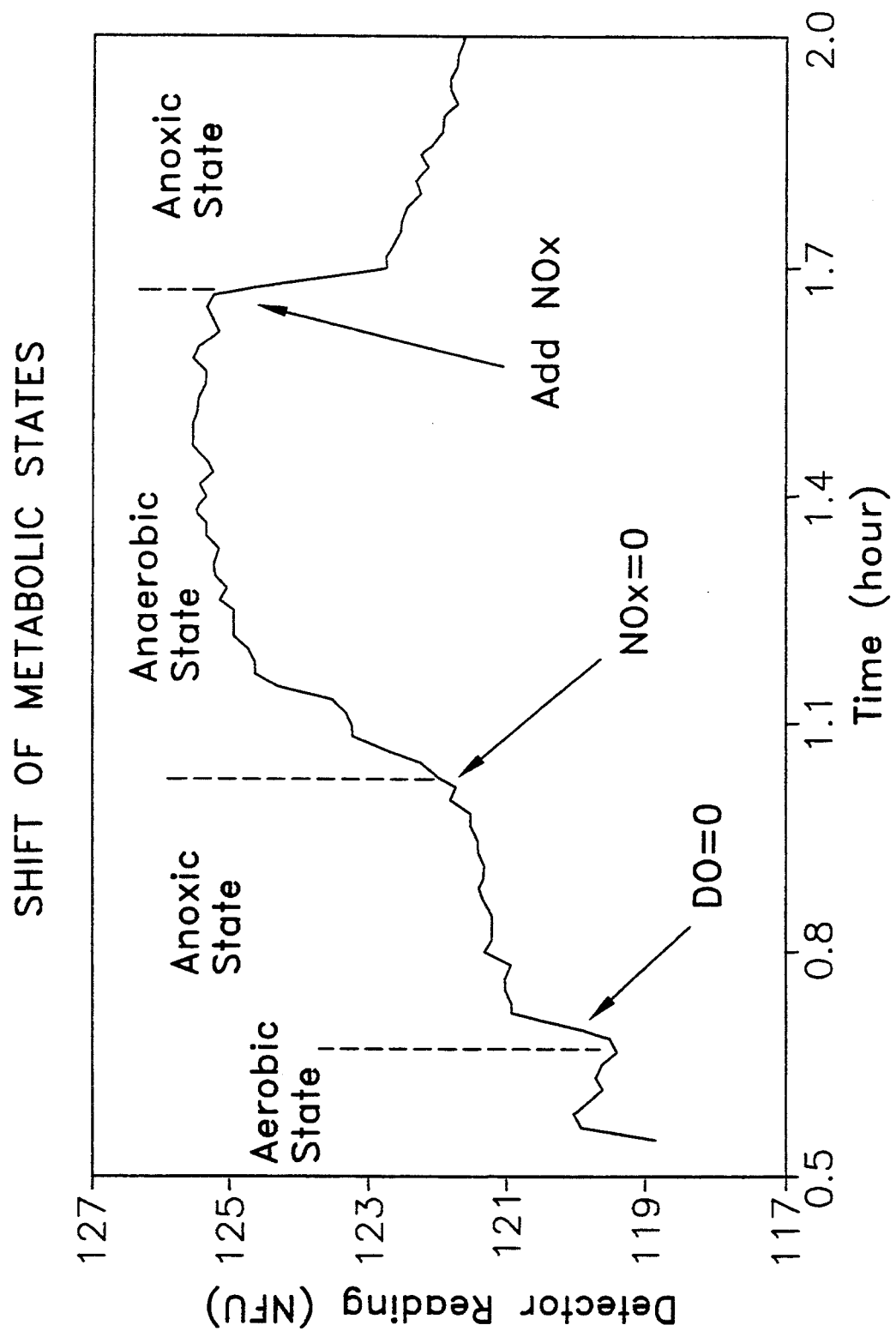
FIG. 2 is a graph depicting the changes in NADH fluorescence during the changes in metabolic activity over a period of time.

The proper evaluation and control of a complex BNR process requires an accurate and current assessment of the metabolic activity of the mixed liquor in a variety of environments and under a number of conditions. Unlike oxygen metabolism, which is only active during the aerobic stage of the BNR process, NADH metabolism is involved in all environmental stages. Thus, NADH is an excellent indicator of metabolic activity that can be used to control the entire BNR process, whereas oxygen metabolism cannot. The dominant organisms and the active biochemical pathways vary with the environmental stages of the bioreactor. However, one common factor is the requirement to transfer energy by the oxidization of available energy sources. Those reactions are summarized in FIG. 1, over the anaerobic, anoxic and oxic stages which shows the role of nicotinamide adenine dinucleotide (NAD+ and NADH) in the energy transfer process.

It is generally believed that under anaerobic conditions the organic materials, such as acetate, for example, are taken up by the cells and converted to acetyl-CoA with the energy for the conversion coming from hydrolysis of intracellular polyphosphate. Acetyl-CoA is further converted to PHB for storage. The reducing power in the form of NADH required for this conversion is obtained by circulating some of the acetyl-CoA through a tricarboxylic acid (TCA) cycle. Also, there may be alternate sources of NADH responsible for this anaerobic conversion of acetyl-CoA to PHB. The concentration of NADH is determined by the balance between the rates of reduction (generation) and oxidization (consumption) reactions. The oxidizing power of the organic compounds involved in the oxidization of NADH in an aerobic fermentation is much weaker than those of nitrate and oxygen. For example, the reduction potential for the oxidization-reduction pair of pyruvate/lactate is $-0.19$ V while those for $NO_3^-/N_2$ and $\frac{1}{2} O_2/H_2O$, are $+0.74$ V and $+0.82$ V, respectively. Consequently, the rate of NADH oxidization is much slower with anaerobic metabolism than with denitrification and respiration. The intracellular level of NADH at the anaerobic stage is therefore higher than those at the anoxic and oxic stages.

In order to effectively control the operation of the BNR process, it is necessary to regulate specific process parameters based upon the biological activity of the microorganisms in the anaerobic, anoxic and oxic stages of the treatment. Wastewater treatment plants are often subjected to severe transient conditions, such as during variations in organic loads. Controlling the treatment process in response to these conditions requires a fast and effective means of measuring biological activity.

The present invention is directed towards an improved method and apparatus for monitoring and controlling biological activity in wastewater treatment systems by detecting changes in the intracellular NADH level of the microorganisms. The apparatus includes a chamber which is opened and closed to capture a sample of mixed liquor. The chamber contains a NADH sensor which detects changes in the biological activity as the mixed liquor shifts its metabolism due to changes in environmental conditions. These real-time changes in biological activity may be monitored and can be used as the input function for driving process and control algorithms to ensure efficient process performance. Such algorithms are known in the art and are not discussed further. It should be noted that the following embodiments of the present invention are for the purpose of illustration only and are not intended to limit the spirit or scope of the invention as defined in the appended claims in any way.

Figure 3:
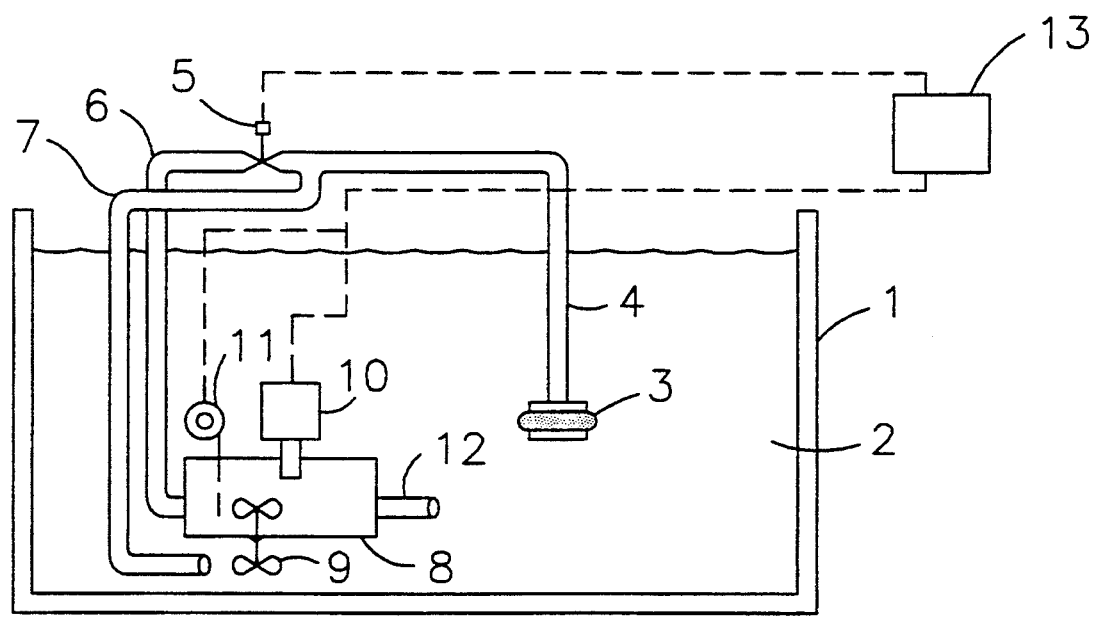
FIG. 3 shows a schematic front elevational view of a preferred embodiment of the invention used to monitor a bioreactor tank.

In a preferred embodiment of the present invention, shown in FIG. 3, bioreactor tank 1 is filled with mixed liquor 2. Pump 3, situated in tank 1, transfers mixed liquor through feed pipe 4 to return pipe 7. Computer/monitor 13, electrically connected to solenoid valve 5, opens solenoid valve 5 to allow a sample of mixed liquor to pass through inlet 6 to detection chamber 8. Agitator 9 mounted on both sides of both detection chamber 8, ensures uniform suspension of microorganisms in the mixed liquor wastewater in detection chamber 8.

Detection probe 10 is positioned in detection chamber 8 and electrically connected to computer/monitor 13 to detect changes in fluorescence of the NADH in the wastewater sample. A preferred detection probe 10 is disclosed in U.S. Pat. No. 4,577,110, which is owned by the assignee hereof and is hereby incorporated by reference. Of course, other apparatus can be employed as a probe so long as the same detection capabilities are available. Computer/monitor 13 may be of any suitable type such as a personal computer or the like. Feeding device 11, also connected to computer/monitor 13, provides nutrients to the microorganisms in the wastewater in detection chamber 8. Outlet 12 connected to detection chamber 8 allows the mixed liquor to be flushed from detection chamber 8 and replaced with a fresh sample.

The preferred operation of the system is as follows. Pump 3 continuously pumps mixed liquor through feed line 4 and return line 7. At a designated time, solenoid valve 5 is activated electronically by a computer connected to computer/monitor 13, which opens the valve to permit a sample of mixed liquor to pass through inlet 6 to detection chamber 8. The solenoid valve 5, which is controlled by computer/monitor 13, shuts off the flow of the mixed liquor to detection chamber 8 after a predetermined amount of sample has passed through feed line 4, return line 7, detection chamber 8 and outlet 12, providing for the complete flushing of detection chamber 8 of a prior sample of mixed liquor and refilling with a new sample of mixed liquor. Of course, outlet 12 is equipped with a suitable blocking device (not shown) to prevent ingress of wastewater into detection chamber 8 through outlet 12.

The mixed liquor resumes its continuous flow through return line 7 after solenoid valve 5 closes. This flow propels agitator 9 which ensures that microorganisms in the sample are suspended uniformly inside detection chamber 8. Uniform suspension assists in achieving an accurate detection of NADH by detection probe 10. Also, depending on the specific application, certain amounts of reagents may be fed to detection chamber 8 at the moment when the chamber is filled with a fresh sample of mixed liquor.

After filling detection chamber 8 with a fresh sample of mixed liquor, the metabolic activity of the sample changes from an aerobic to an anoxic to an anaerobic condition as time elapses. The time intervals that the sample spends in the aerobic, anoxic and anaerobic states, and the changes in the intracellular NADH corresponding to these changes in metabolic activity, may be detected by probe 10, registered and analyzed by computer 13. The use of computer 13 allows for the real-time, on-line monitoring of the biological activity in detection chamber 8. Interpretation of the information obtained by the present invention depends on its specific application and installation location in the WWTP. The design of the present invention may be modified to meet the specific requirements of the wastewater treatment plant and its location.

Figure 8:
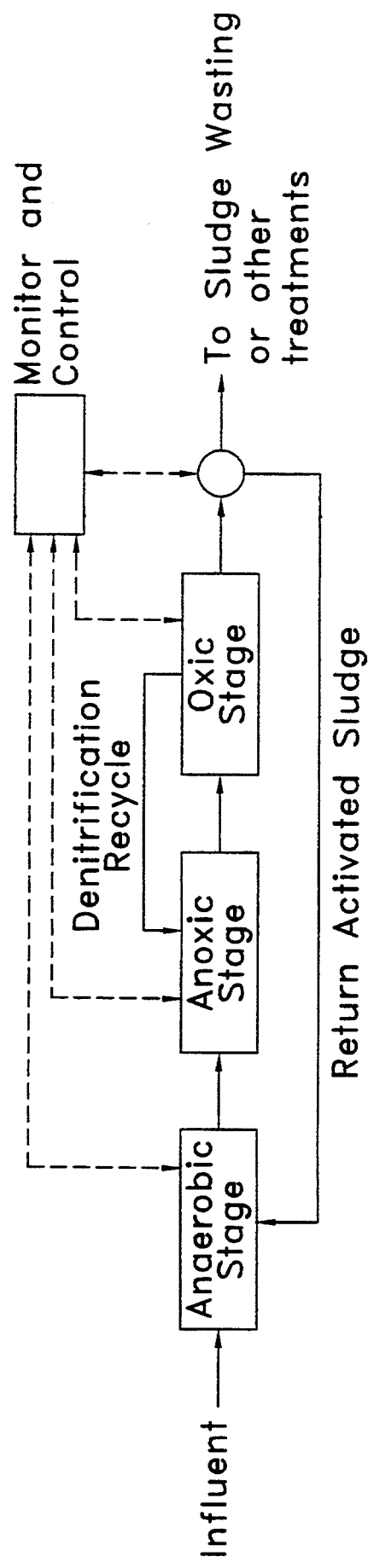
FIG. 8 is a schematic of the monitoring of a typical wastewater treatment process utilizing embodiments of the present invention.

The apparatus and method for monitoring biological activity can be used in all stages of a WWTP or any combination thereof. Incorporation of the apparatus and method for monitoring biological activity into a typical WWTP is shown schematically in FIG. 8. The general application and use of the apparatus shown in FIG. 3 in the anaerobic, anoxic and/or aerobic stages of a typical wastewater treatment plant will now be discussed.

1. Use in the anaerobic stage

Figure 4:
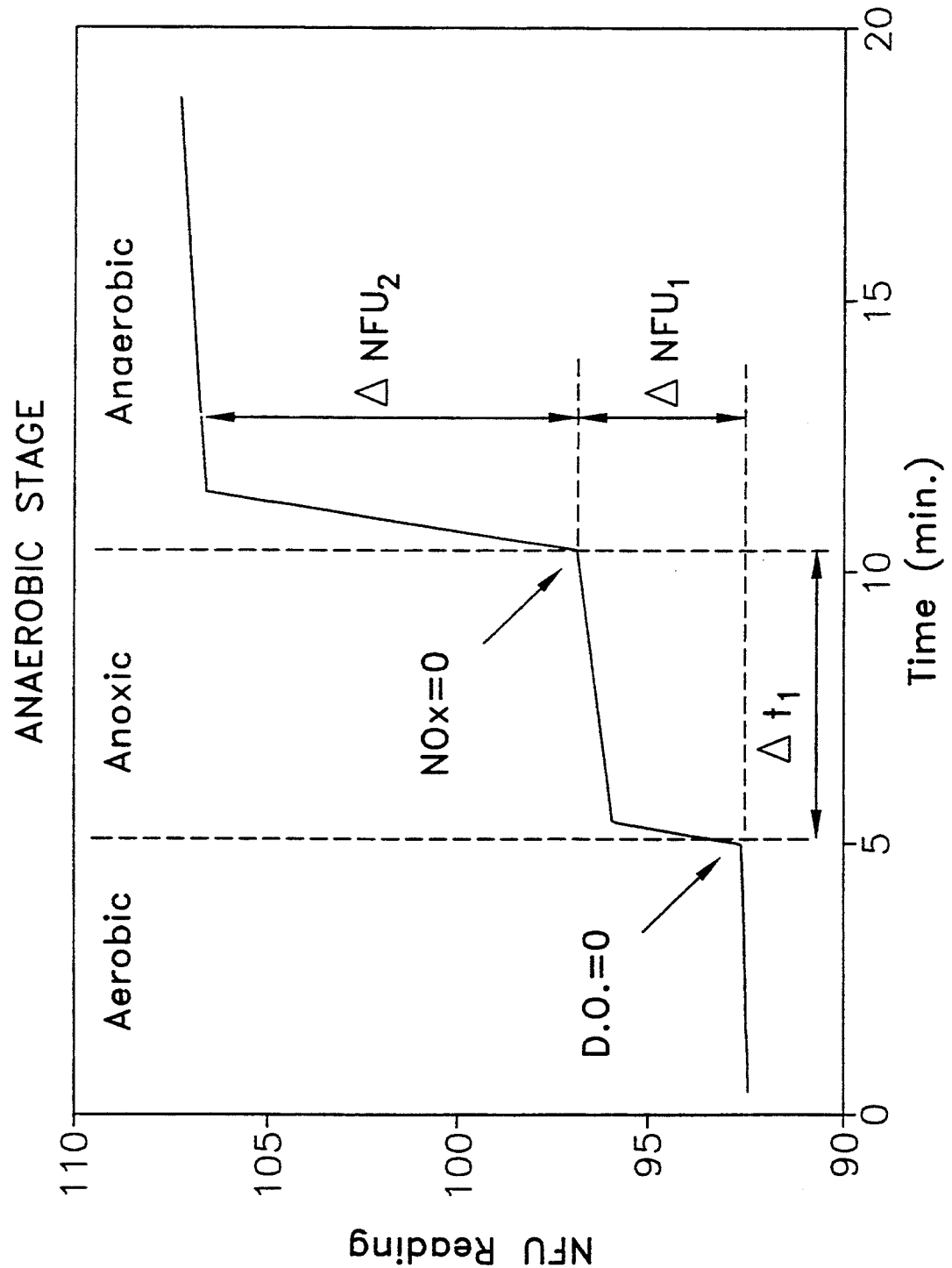
FIG. 4 is a graph of an operational profile depicting changes in NADH fluorescence over time from an anaerobic stage of treatment.

The operational profile of the biological activity monitoring apparatus when installed in the anaerobic stage of a WWTP is illustrated in FIG. 4. The term NFU, as shown in FIG. 4 and as used hereinafter, represents a normalized or relative quantity or level of NADH fluorescence. Three parameters, $\Delta NFU_1$, $\Delta NFU_2$, and $\Delta t_1$ are analyzed for the evaluation of the biological activity of the microorganisms. $\Delta NFU$ represents the total increase in NADH concentration; $\Delta NFU_1$ represents the first step increase of NADH concentration; $\Delta NFU_2$ represents the second step increase of NADH concentration; and $\Delta t_1$ represents the time period of the anoxic portion during the anaerobic stage of the WWTP. The overall change in NADH concentration through the aerobic, anoxic and anaerobic states of the mixed liquor from the anaerobic stage of treatment can be expressed according to the equation:

$$\Delta NFU = \Delta NFU_1 + \Delta NFU_2$$

$\Delta NFU$ is proportional to the overall biomass concentration in the sample. Although the absolute value of the biomass concentration cannot be determined from a single measurement, it is possible to accurately and reliably estimate the population distribution of the denitrifying and non-denitrifying microorganisms by methods known in the art. When the concentration of dissolved oxygen in the sample decreases to below a critical value and is finally depleted, those microorganisms that cannot use nitrate and/or nitrite as electron acceptors switch to an anaerobic state, shifting the mixed liquor from an aerobic to an anoxic state. This corresponds to the first NADH increase, $\Delta NFU_1$. The majority of microorganisms which cannot perform denitrification are autotrophic nitrifiers, such as Nitrosomonas and Nitrobacter. Therefore, the value of $\Delta NFU_1/\Delta NFU$ is proportional to the percentage of nitrifiers in the overall biomass population. Conversely, those microorganisms that are capable of performing denitrification consume all the nitrate in the sample before entering an anaerobic state.

The second step increase in NADH, $\Delta NFU_2$, from the sample corresponds to a shift in the sample from an anoxic to an anaerobic state. Therefore, the value of $\Delta NFU_2/\Delta NFU$ is proportional to the percentage of denitrifiers in the overall biomass population.

One possible application of the biological activity monitoring apparatus in the anaerobic stage of a WWTP is to determine the efficiency of $NH_3$ removal. When the value of $\Delta NFU_1/\Delta NFU$ is below a predetermined value, the population of nitrifiers in the bioreactor tank is lower than the required amount for proper $NH_3$ removal. Changing operational parameters, such as increasing hydraulic retention time or increasing the RAS flow rate, for example, is helpful in modifying the process to make the WWTP more efficient. If the alteration of the return activated sludge (RAS) flow rate parameter is adopted, it should be continued until the value of $\Delta NFU_1$ reaches a set point so that the population of nitrifiers is large enough to maintain the proper nitrification rate.

$\Delta t_1$ is the time the mixed liquor spends in the denitrification stage before the sample shifts to the anaerobic state. When $\Delta t$ represents the hydraulic retention time of the mixed liquor in the anaerobic stage of bioreactor tank 1, then the ratio of $\Delta t_1/\Delta t$ indicates that a fraction of the bioreactor is used for denitrification within the whole anaerobic stage in the WWTP.

2. Use in the Anoxic Stage

Figure 5:
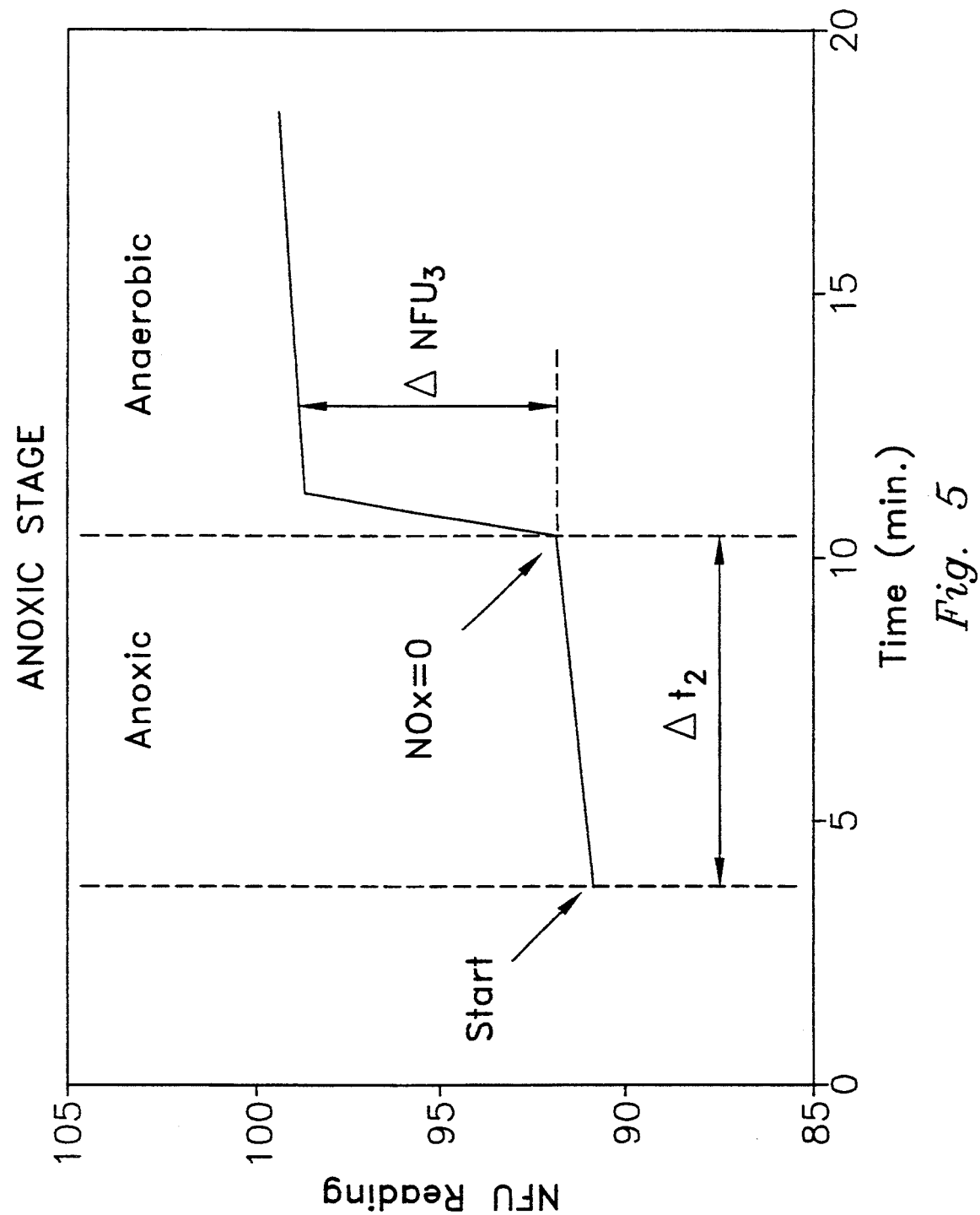
FIG. 5 is a graph of an operational profile depicting changes in NADH fluorescence over time from an anoxic stage of treatment.

The operational profile of the biological activity monitoring apparatus when used in the anoxic stage of a WWTP is illustrated in FIG. 5. Two parameters, $\Delta NFU_3$, which represents the change in NADH fluorescence during the anaerobic state of the sample, and $\Delta t_2$, which represents the length of time in minutes of the anoxic state of the sample, are useful in monitoring and controlling the anoxic stage of a WWTP.

The value of $\Delta t_2$ is measured as the time period from capture of the sample in detector chamber 8 to the moment when denitrification is completed. The value of $\Delta t_2$ can be used to evaluate whether the hydraulic retention time in the whole anoxic stage, $T_{den}$, is long enough for the denitrification process to be completed. The ideal time is $T_{den} = \Delta t_2$. To approach this ideal denitrification time, the internal recycling rate can be adjusted accordingly.

3. Use in the Oxic Stage

Figure 6:
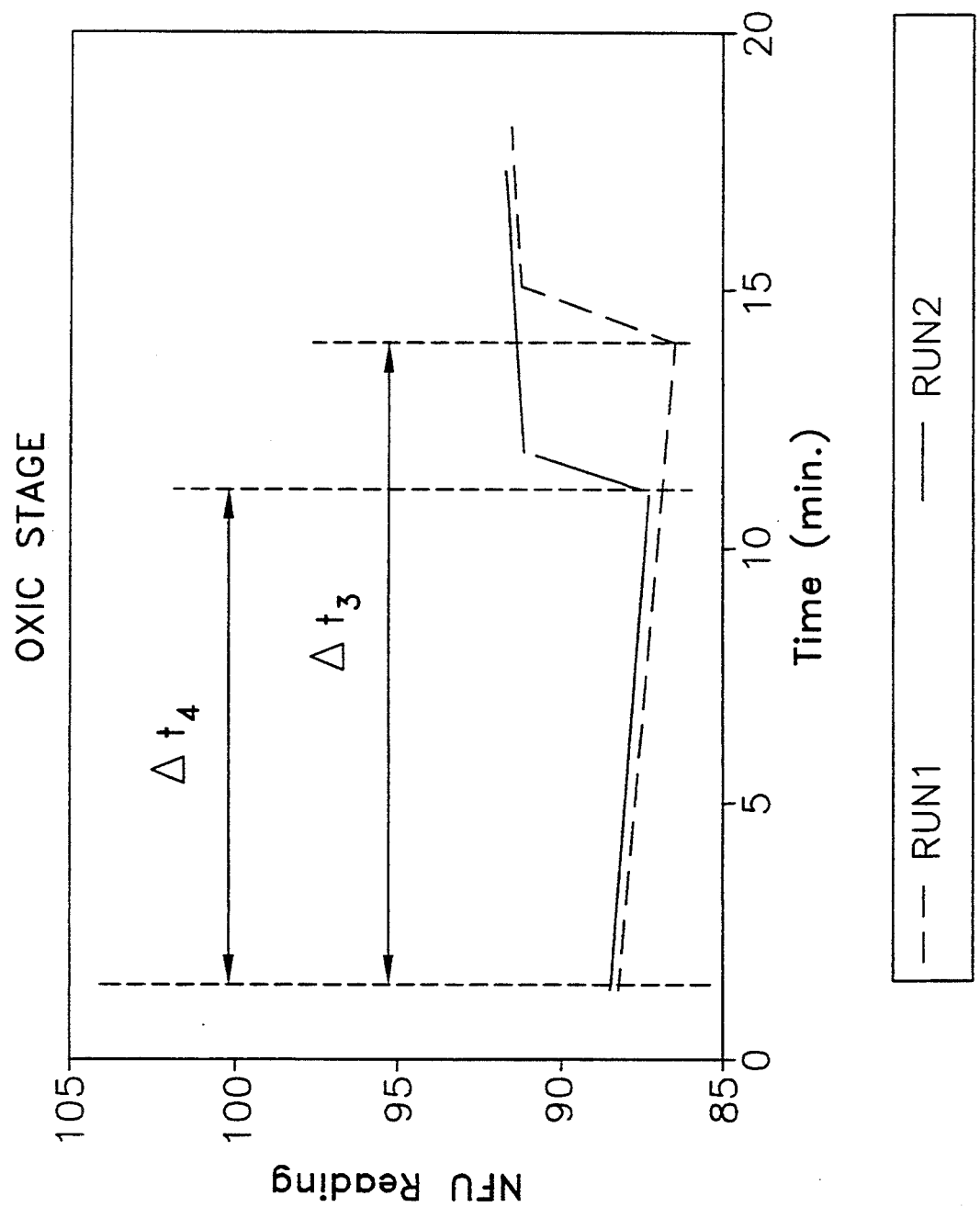
FIG. 6 is a graph of an operational profile depicting the changes in NADH fluorescence over time from an oxic stage of treatment.

An operation profile for the use of the apparatus in the oxic stage of a WWTP is illustrated in FIG. 6. Since the degradation of pollutants is almost completed, the BOD concentration is very low, and the change in fluorescence of NADH concentration corresponding to the metabolic shift of the captured sample from an aerobic to an anoxic state is very small, but nevertheless detectable.

One of the applications of the present invention in the oxic stage is to serve as a $NH_3$ meter. This aspect preferably operates as follows: Two sets of monitoring apparatus (not shown) may be used in the same location in bioreactor tank 10. Both detection chambers 8 are filled with mixed liquor samples at the same time. For the first chamber, $\Delta t_3$ represents the time from capturing the sample to the start of the anoxic state of the sample registered by computer 13. In the second chamber, immediately after the chamber is filled with mixed liquor, a certain amount of $NH_3$ is added, for example 0.5 ppm, from the feeding device 11. The time, $\Delta t_4$, from capturing the sample in chamber 8 to the start of the anoxic state of the wastewater in the detection chamber 8 is then registered.

Figure 7:
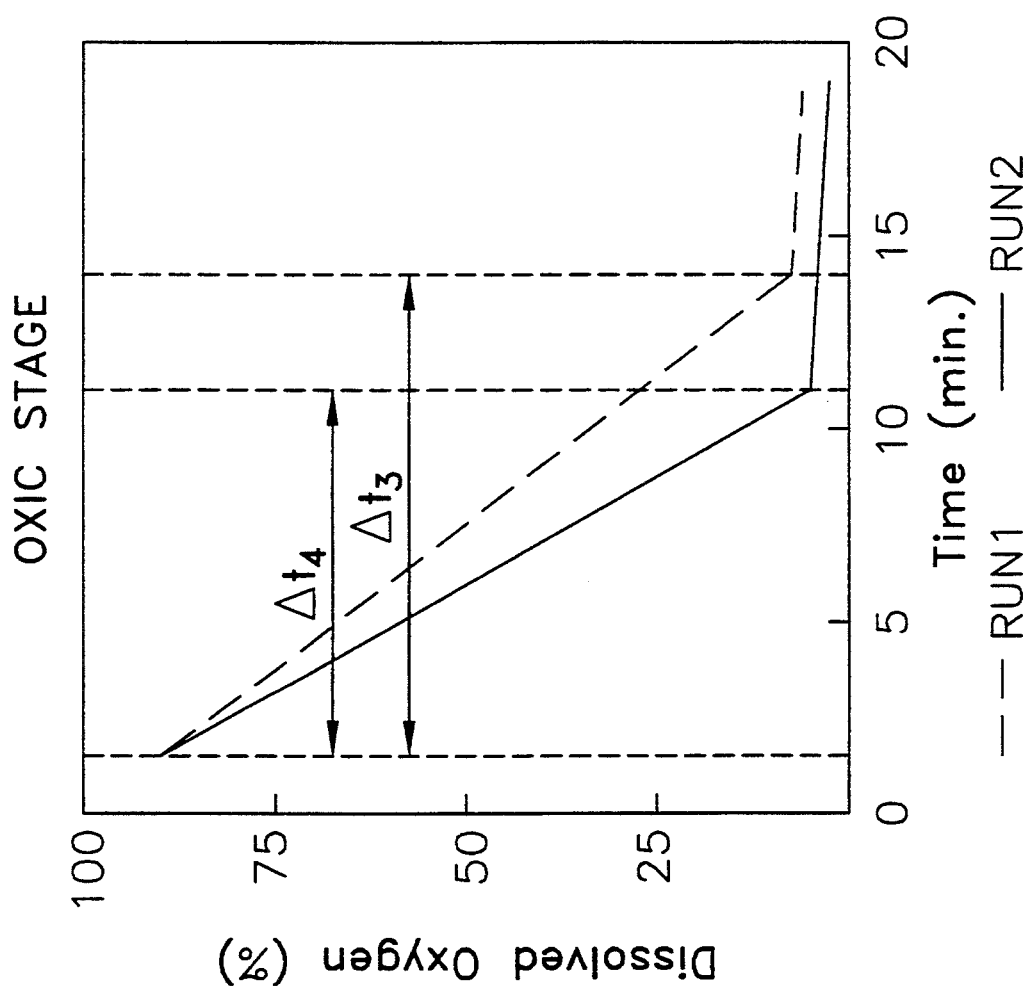
FIG. 7 is a graph of an operational profile depicting the changes in percentage of dissolved oxygen over time from an oxic stage of treatment.

In order to determine the $NH_3$ concentration, it is assumed that the dissolved oxygen (D.O.) consumption in the oxic stage is mostly due to the nitrification process. A typical operational profile for the consumption of dissolved oxygen during the oxic stage is illustrated in FIG. 7. Experimental results performed indicate that the oxygen consumption rate of the mixed liquor changed negligibly when acetate and glucose (5 ppm) were added to the system with feeding device 11, while significant change was observed when 0.1 ppm of $NH_3$ was added to the system.

The concentration of $NH_3$ in the oxic state of the WWTP is expressed as:

$$(NH_3)_1 = \Delta NH_3 \, \Delta t_4 / (\Delta t_3 - \Delta t_4)$$

Where $(NH_3)_1$ is the ammonia concentration in the water phase at the end of the oxic stage, $\Delta NH_3$ is the known amount of ammonia added to the second detection chamber, respectively. The present invention can be used in the oxic state of a WWTP to accurately monitor the $NH_3$ concentration in the bioreactor tank. Various system parameters, such as retention time, can then be altered to enhance the nitrification process and, if necessary, to increase the efficiency of the waste water treatment system.

In the method according to the invention, information about biomass composition, efficiency of denitrification, nitrification and BOD removal processes and $NH_3$ concentration in the oxic stage of a WWTP can be obtained. This information may be monitored and analyzed by computer 13 which evaluates the biological activity in the anaerobic, anoxic and aerobic stages of a WWTP and can alter system parameters such as the RAS flow rate, the oxygen supply rate, the internal recycling rate or the hydraulic residence time or the like to maximize the efficiency of the WWTP in response to transient conditions or normal operation.

Although the invention has been illustrated by use of specific embodiments thereof, it should be noted that the present invention is not limited in spirit or scope as defined in the appended claims. For example, the present invention can be used to monitor various parameters of the individual aerobic, anoxic and anaerobic stages of a wastewater treatment plant individually, or the invention can be used to monitor and control the entire WWTP operation in maximizing the efficiency thereof. Additionally, individual components of the invention may utilize equivalent substitutions. For example, the sample in detection chamber 8 may be uniformly suspended by use of any means of controllable agitation. The filling of the detection chamber with a predetermined amount of wastewater may be performed by a means other than a feed line, a solenoid valve, an inlet line and a return line. The monitoring system may consist of a personal computer with applicable software or individual electronic meters to be analyzed separately, all of which are known in the art. Other possible embodiments and modifications of the present invention in keeping with the spirit and skills thereof, will be obvious to one of ordinary skill in the art.

It should also be emphasized that although emphasis has been placed on measurement of NADH fluorescence to determine the quantity or concentration of NADH, this emphasis is simply the preferred manner in which NADH quantity or concentration is determined. Other means and methods for accomplishing this task are fully contemplated as falling within the scope of this invention. For example, NADH quantity or concentration may be determined by use of biochemical assays, such as those sensitive to NADH. Such assays are known in the art and typically employ enzymes and substrate components to assist in the assay. Still other means known and not yet developed can be used so long as they are capable of determining the presence of NADH.

What is claimed is:

1. A method for monitoring biological activity in a wastewater treatment process comprising the steps of:
    in situ separating and isolating wastewater samples from wastewater in said wastewater treatment process;
    irradiating said samples with radiation of a selected wavelength;
    detecting changes in fluorescence emitted by NADH from microorganisms contained within said samples in response to said radiation; and
    analyzing the changes in NADH fluorescence to determine status of selected sample characteristics.

2. The method defined in claim 1 wherein said sample characteristics are selected from the group consisting of biomass quantity, biomass composition, efficiency of denitrification, nitrification, $NH_3$ concentration, biological oxygen demand and supply of oxygen.

3. The method of claim 1 further comprising the step of returning said samples to said wastewater treatment process.

4. A method for monitoring and controlling biological activity in a wastewater treatment process employing return activated sludge comprising the steps of:
    sampling and isolating wastewater from anaerobic, anoxic and/or aerobic stages of said treatment process;

irradiating said sample with radiation of a selected wavelength;

detecting changes in fluorescence emitted by NADH from microorganisms contained within said sample;

analyzing said changes to determine status of selected sample characteristics;

controlling selected process parameters in said treatment process depending on the status of said selected sample.

5. The method defined in claim 4 wherein said sample characteristics are selected from the group consisting of biomass quantity, biomass composition, efficiency of denitrification, nitrification, $NH_3$ concentration, biological oxygen demand and supply of oxygen.

6. The method defined in claim 4 wherein said process parameters are selected from the group consisting of return activated sludge flow rate, internal recycling rate, oxygen supply rate and hydraulic residence time.

7. A method of monitoring and controlling biological activity in a wastewater treatment process comprising:

sampling and isolating wastewater portions, in situ, from wastewater in said wastewater treatment process;

measuring the quantity of NADH in microorganisms contained within samples of said wastewater;

analyzing changes in the quantity of said NADH;

controlling selected process parameters in said treatment process in response to said changes.

8. The method defined in claim 7 wherein said analyzing step determines selected sample characteristics.

9. The method defined in claim 8 wherein said sample characteristics are selected from the group consisting of biomass quantity, biomass composition, efficiency of denitrification, nitrification, $NH_3$ concentration, biological oxygen demand and supply of oxygen.

10. The method defined in claim 7 wherein said process parameters are selected from the group consisting of return activated sludge flow rate, internal recycling rate, oxygen supply rate and hydraulic residence time.

11. A method of monitoring and controlling biological activity in a wastewater treatment process comprising:

isolating wastewater portions, in situ, from wastewater in said wastewater treatment process;

measuring NADH in microorganisms contained within said isolated portions of wastewater;

analyzing changes in said NADH;

controlling selected process parameters in said treatment process in response to said changes.

12. A method of monitoring and controlling biological activity in a wastewater treatment process comprising:

in situ isolating wastewater portions from wastewater in said wastewater treatment process;

measuring NADH in microorganisms contained within said isolated portions of wastewater;

analyzing changes in said NADH caused by shifts in biological activity of said microorganisms;

controlling selected process parameters in said treatment process in response to said changes.

13. A method for monitoring biological activity in a wastewater treatment process comprising the steps of:

isolating wastewater samples, in situ, from wastewater in said wastewater treatment process;

detecting changes in NADH from microorganisms contained within said isolated samples caused by shifts in biological activity of said microorganisms; and analyzing the changes in NADH to determine status of selected sample characteristics.

* * * * *

UNITED STATES PATENT AND TRADEMARK OFFICE
CERTIFICATE OF CORRECTION

PATENT NO. : 5,401,412
DATED : March 28, 1995
INVENTOR(S) : Xin Yang, Jaw F. Lee, William B. Armiger and Sergey K. Maneshin It is certified that error appears in the above-indentified patent and that said Letters Patent is hereby corrected as shown below:

In the Abstract, line 4, please change "AND(P)H" to --NAD(P)H--.

In Column 6, line 55, please change "At" to --Δt--.

Signed and Sealed this

Thirtieth Day of May, 1995

BRUCE LEHMAN

Attest:

Attesting Officer

Commissioner of Patents and Trademarks